United States Patent [19]

Okada

[11] Patent Number: 4,726,355
[45] Date of Patent: Feb. 23, 1988

[54] CURVABLE PART DEVICE FOR ENDOSCOPE DEVICES

[75] Inventor: Minoru Okada, Hachioji, Japan

[73] Assignee: Olympus Optical Co., Ltd., Tokyo, Japan

[21] Appl. No.: 15,461

[22] Filed: Feb. 17, 1987

[30] Foreign Application Priority Data

Feb. 17, 1986 [JP] Japan ................. 61-032482

[51] Int. Cl.⁴ .......................... A61B 1/00; F16L 11/18
[52] U.S. Cl. ......................................... 128/4; 138/120
[58] Field of Search ................. 128/4, 6; 138/120

[56] References Cited

U.S. PATENT DOCUMENTS

| | | | |
|---|---|---|---|
| 3,060,972 | 10/1962 | Sheldon | 138/120 |
| 3,071,161 | 1/1963 | Ulrich | 138/120 |
| 3,583,393 | 6/1971 | Takahashi | 128/4 |
| 3,799,151 | 3/1974 | Fukaumi et al. | 128/6 |
| 4,108,211 | 8/1978 | Tanaka | 138/120 |
| 4,351,323 | 9/1982 | Ouchi et al. | 128/4 |
| 4,432,349 | 2/1984 | Oshiro | 128/4 |
| 4,530,568 | 7/1985 | Haduch et al. | 128/6 X |
| 4,659,195 | 4/1987 | D'Amilio et al. | 128/4 X |
| 4,686,963 | 8/1987 | Cohen et al. | 128/4 |

FOREIGN PATENT DOCUMENTS 56-89233 12/1981 Japan .
57-157302 12/1982 Japan .

Primary Examiner—William H. Grieb
Attorney, Agent, or Firm—Armstrong, Nikaido, Marmelstein & Kubovcik

[57] ABSTRACT

In the insertion part of at least one of an endoscope and an endoscope auxiliary inserted through this endoscope, guide wire receivers for curving wires passed through curvably jointed knot rings formed on the tip side of the insertion part are engaged and fixed respectively within incisions formed in the knot rings.

6 Claims, 12 Drawing Figures

A
CURVABLE PART DEVICE FOR ENDOSCOPE DEVICES

FIELD OF THE INVENTION AND RELATED ART STATEMENT

This invention relates to a curvable part device for endoscope developed wherein the effective cross-sectional area of the curvable part is made wider.

Recently, there have come to be extensively used endoscope whereby an affected part or the like within a body cavity can be observed and diagnosed or can be treated with treating tools by inserting an elongated insertion part into the depths of the body cavity through such inserting course as a mouth without incising the body.

In the industrial field, too, endoscopes are used extensively in such case as of inspecting the interior of a jet engine or of a pipe cavity in a chemical plant.

Among such endoscopes as are mentioned above, there are a rigid endoscope wherein the insertion part is rigid and a flexible endoscope wherein the insertion part is flexible and can be inserted through a curved course.

In the case of the above mentioned flexible endoscope, generally a curvable part is provided near the tip of the insertion part so as to be able to be curved and operated in the operating part on the holding side.

For the above mentioned curvable part, there is a related art example disclosed, for example, by the present applicant in the gazette of Japanese utility model laid open No. 157302/1982. In this art example, knot rings are jointed, one of operating wires extended through inside the jointed knot rings to a rear operating part is pulled and the operating wire on the other side is relaxed so that the jointed knot rings may be curvable vertically or horizontally.

The above mentioned operating wires are passed through inserting tubes (of guide rings) as receivers for the wires fitted to the inside surfaces of the knot rings.

In the above mentioned art example, as the guide rings for passing the wires are provided inside the knot rings, the effective cross-sectional area of the hollow path inside the knot ring is so small that it is hard to pass light guide fibers or image guide fibers through the hollow path. Therefore, the knot rings must be made so large in the diameter and the insertion part becomes so large in the outside diameter that, in case the insertion part is to be inserted into a body cavity, a great pain will be forced to the patient. If the insertion part is large in the outside diameter, its inserted uses will be restricted undesirably.

Another related art example is disclosed by the present applicant in the gazette of Japanese patent laid open No. 89233/1981. In this art example, incisions are provided in the knot rings so as to make it easy to fit guide rings. The same as in the above mentioned first art example, the incisions in this case do not enlarge the effective cross-sectional area of the hollow path inside the knot rings and do not solve the above mentioned defects.

OBJECTS AND SUMMARY OF THE INVENTION

An object of the present invention is to provide a curvable part device for endoscope devices wherein the effective cross-sectional area inside the knot rings can be made larger without enlarging the outside diameter of the knot rings.

Another object of the present invention is to provide a curvable part device for endoscope devices wherein the insertion part in which a curvable part is formed can be made smaller in the diameter and the using range is wider.

In the curvable part device of the present invention, wires for the curving operation are passed, guide rings functioning as wire receivers holding the wires so as to be free to advance and retreat are fitted to knot rings, slits along the longitudinal direction of the insertion part are incised in the knot rings and guide rings are fixed as fitted respectively in the slits so as to reduce the area of the parts of the guide rings projecting inside the knot rings and to increase the effective cross-sectional area inside the knot rings.

BRIEF DESCRIPTION OF THE DRAWINGS

FIG. 1 is a sectioned view showing wire receivers as secured to knot rings forming the curvable part of the first embodiment.

FIG. 2 is a perspective view showing an endoscope provided with the first embodiment.

FIG. 3 is a sectioned view showing the curvable part of the first embodiment.

FIG. 4 is a magnified sectioned view on line A—A' in FIG. 3.

FIG. 5 is a magnified sectioned view on line C—C' in FIG. 3.

FIG. 6 is a sectioned view showing the shape of a wire receiver.

FIG. 7 is a partly sectioned side view showing incisions for fixing wire receivers.

FIG. 8 is a sectioned view showing the insertion part side.

FIG. 9 is a sectioned view on line D—D' in FIG. 8.

DETAILED DESCRIPTION OF PREFERRED EMBODIMENTS

Figure 2:
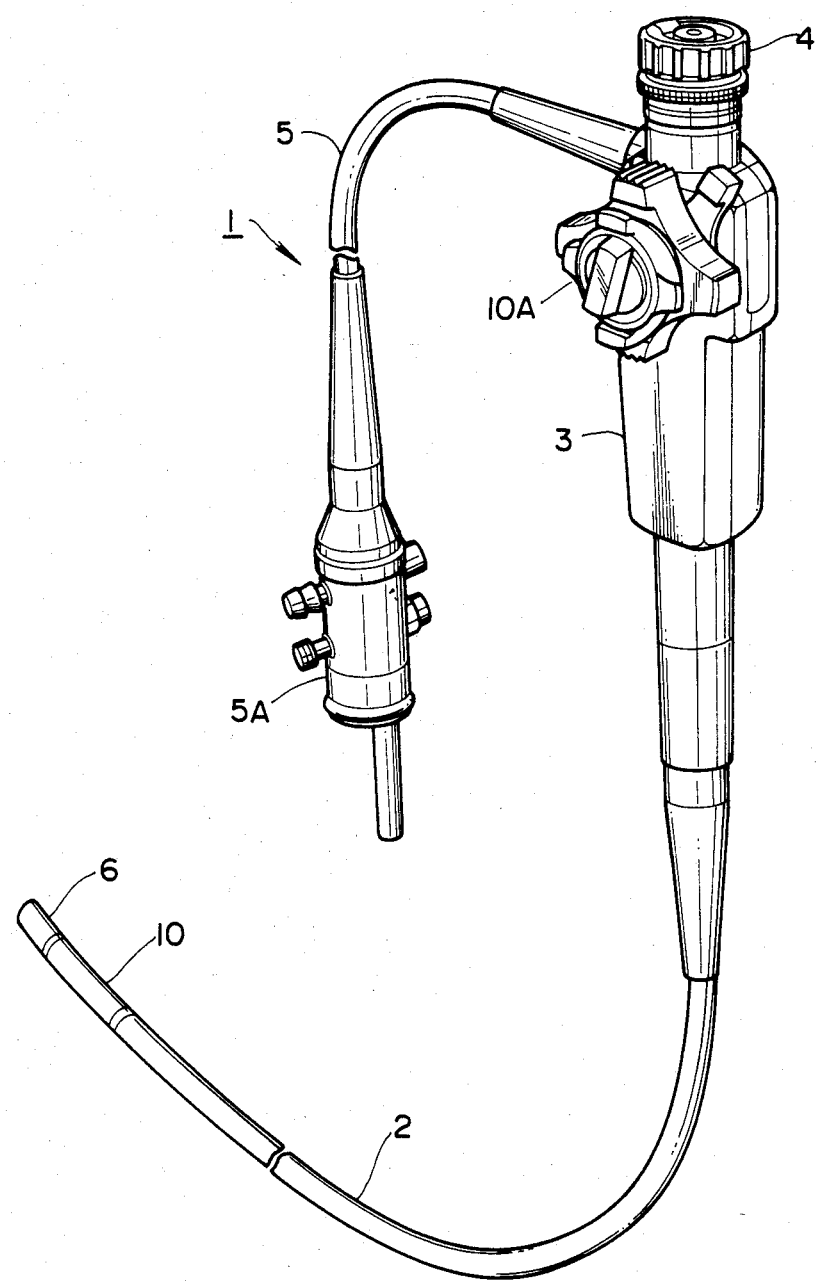

As shown in FIG. 2, an industrial endoscope provided with the first embodiment is formed of an elongated flexible insertion part 2 so as to be insertable into a pipe or the like, a wide operating part 3 connected to the rear end side of this insertion part 2, an eyepiece part 4 connected to the rear end of this operating part 3 and containing an eyepiece and a light guide cable 5 for transmitting an illuminating light and provided to project on the side part of the above mentioned operating part 3.

Figure 3:
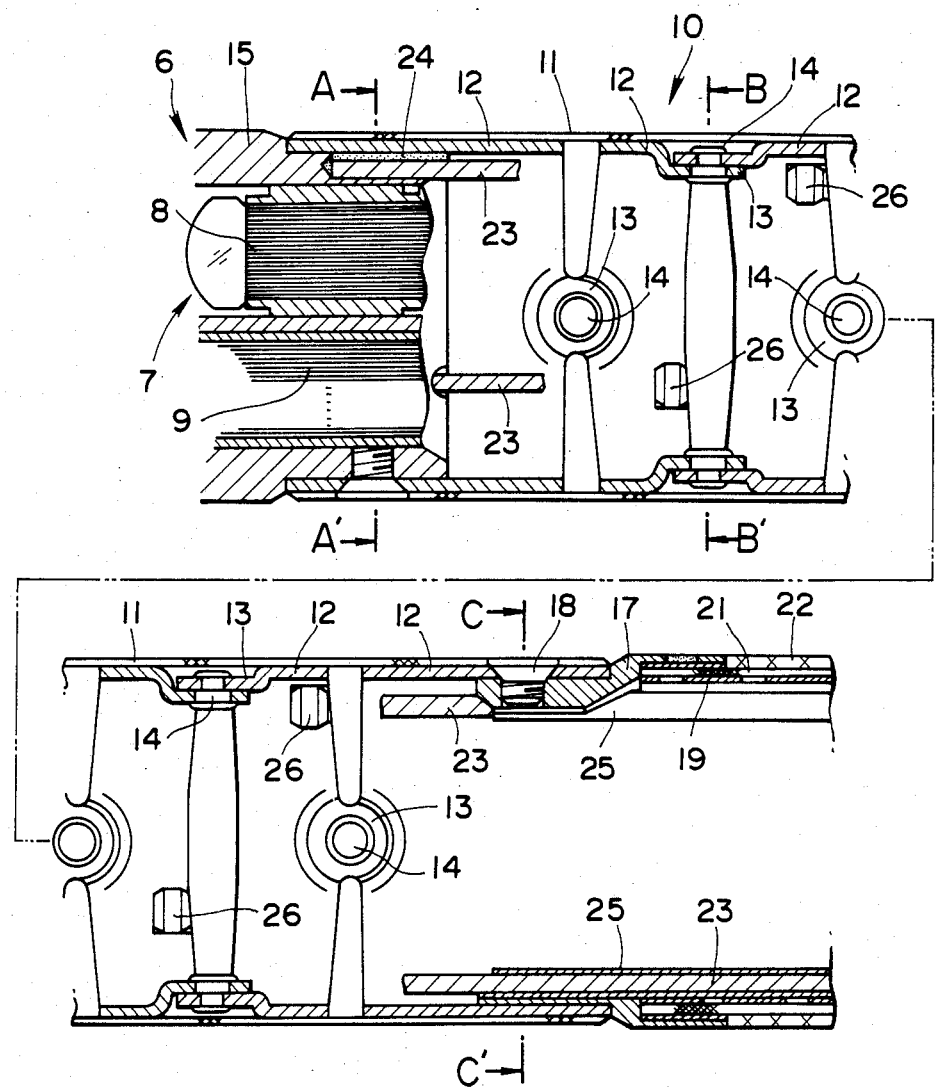

The above mentioned insertion part 2 containes within the tip part 6 an obective system 7 (a part of it is shown in FIG. 3) for forming the image of an object so that an optical image formed by this objective system 7 may be transmitted through an image guide 8 formed of a fiber bundle to the rear end of this image guide and may be magnified and observed through the eyepiece. Within this tip part 6, the exit end of a fiber bundle forming a light guide 9 transmitting an illuminating light is fixed so that the illuminating light of an illuminating lamp within a light source device fitted with a connector 5A of the above mentioned light guide cable 5 may be transmitted and may be emitted on the side of an object to be imaged by the above mentioned objective system 7 to illuminate the object.

A curvable part (device) 10 is formed in the part adjacent to the above mentioned tip part 6 and is made curvable vertically and horizontally by a curving operation knob 10A provided to project on the operating part 3.

Now, the above mentioned curvable part 10 is of such structure as is shown in FIG. 3.

Many annular knot rings 12 are contained inside the part covered with a net tube (blade) 11 and rivets 14 are pivoted in communicating holes of connecting parts 13 projected to be opposed to each other as displaced by 180 degrees in the peripheral direction between the adjacent knot rings 12 to be rotatably fitted.

Figure 4:
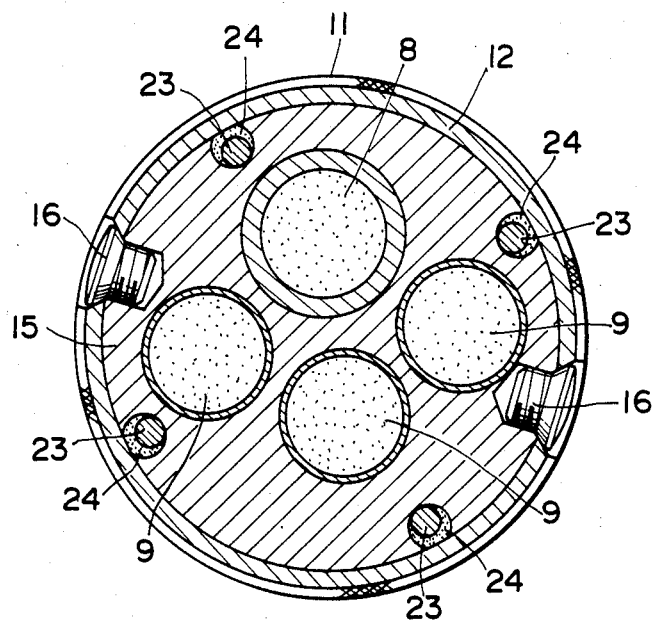
Figure 5:
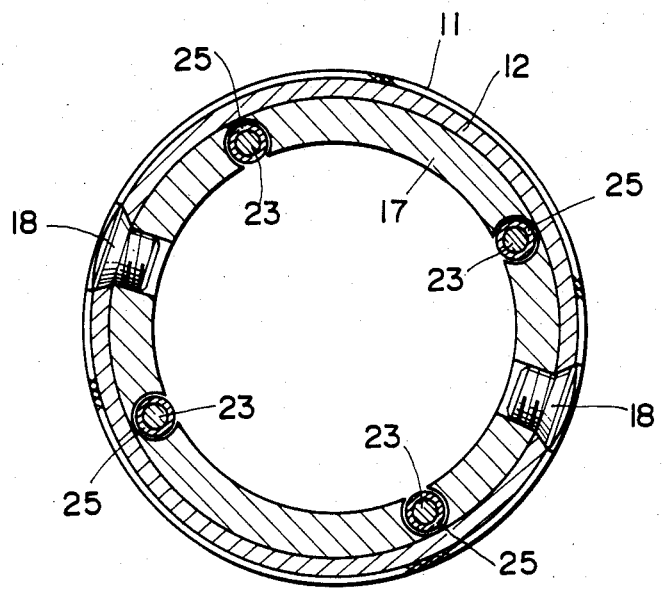

In the above mentioned connecting parts 13, the positions opposed to each other in the horizontal direction (in the direction vertical to the paper surface in FIG. 3) and the positions opposed to each other in the vertical direction are alternately repeated in the longitudinal direction of the curvable part 10. The knot ring 12 in the foremost step is fitted to the outer peripheral surface of the tip part body 15 and is secured to the tip part body 15 with screws 16 as shown in FIG. 4. (By the way, the image guide 8 and light guides 9 are omitted in the respective sectioned views in FIGS. 1 and 5.) The knot ring 12 in the rearmost step is externally fitted to a fixing ring 17 and is fixed together with the net tube 11 with screws 18 as shown in FIG. 5. Inside the rear side of this fixing ring 17, a spiral tube 19 and a net tube 21 outside it are fixed by pouring a solder or the like into the holes of the ring 17. The outer peripheral surface of this net tube 21 is covered with a flexible tube 22.

Now, four wires 23 for the curving operation are passed inside the above mentioned many knot rings 12 jointed in the longitudinal direction of the curvable part 10. The front ends of these wires 23 are contained in recesses or grooves provided in the axial direction on the outer peripheral surface of the above mentioned tip part body 15 and are secured with a solder 15 or the like. The respective wires 23 are covered with stainless steel pipes 25 near the rear end of the curvable part 10. These stainless steel pipes 25 are passed through the ring 17 (See FIG. 5), are inserted through the insertion part 2 and are connected to a curving operation mechanism within the operating part 3. This curving operation mechanism is fundamentally of a structure (not illustrated) of a pair of wires fixed to the outer periphery of a pulley. The above mentioned pulley is rotated by rotating the curving operation knob 10A projected out of the operating part 3. With the rotation of this pulley, one of the wires 23 opposed to each other in the vertical or horizontal direction will be pulled and the other wire 23 will be relaxed so that the pivoting position on the pulled side (in the case of being curved) may be inside to curve the curvable part.

The respective wires 23 passed inside the above mentioned respective knot rings 12 are passed through the inserting holes of wire receivers 26 fitted inside the knot rings 12 to prevent the positions of the wires 23 from moving unstably in the radial direction of the knot rings 12.

Figure 6:
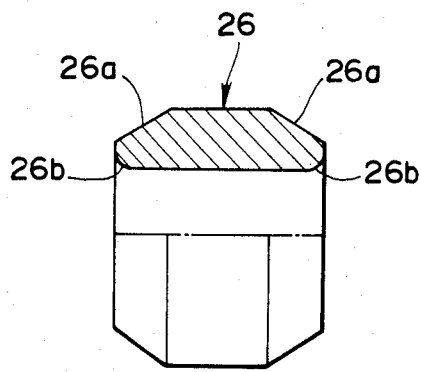

Now, in each wire receiver 26, as shown in FIG. 6, the outer peripheries at both ends of a substantially cylindrical form are incised to form chamfers 26a and both ends of the inserting hole through which the wire 23 is to be inserted are also formed to be chamfers 26b.

Figure 1:
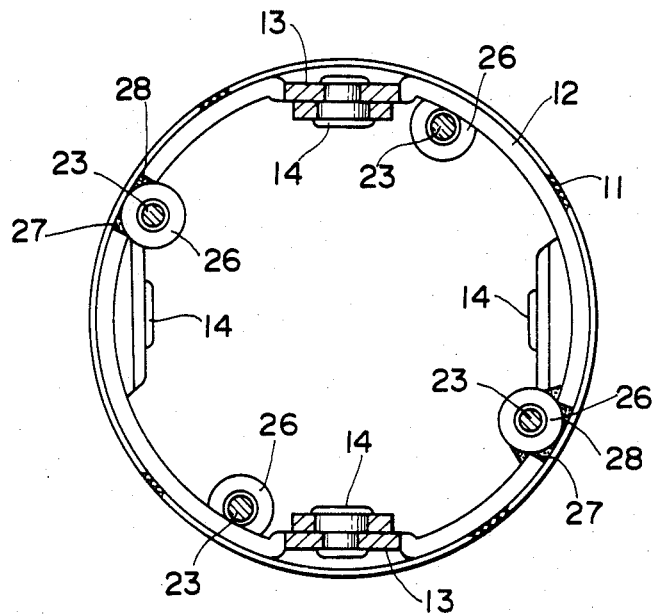
FIGS. 1 to 9 relate to an endoscope provided with the first embodiment of the present invention.
Figure 7:
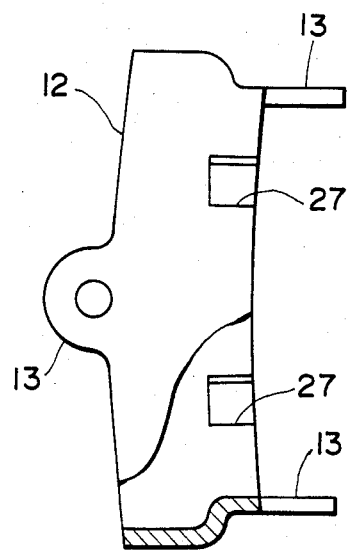

Each knot ring 12 to be fitted with the above mentioned wire receivers 26 is provided with incisions 27 in the positions opposed to each other as displaced by an angle of 180 degrees as shown in FIG. 7, the wire receivers 26 are secured by soldering 28 in the respective incisions 27 and the wires 23 are passed respectively through the secured wire receivers 26 as shown in FIG. 1.

That is to say, the width (in the peripheral direction of the knot ring 12) of each incision 27 is so set that the outer peripheral surface of the wire receiver 26 put (or fitted) in the incision 27 may be flush or in contact with the outer peripheral surface of the knot ring 12. It is a feature that, as the wire receivers are secured in this state, the effective radius inside the knot ring 12 can be made larger by the thickness of the knot ring 12 or wire receiver 26 than in the case of securing the wire receivers on the inner peripheral surface of the knot ring 12 without providing the incisions 17 or in the case of securing the wire receivers provided with fitting parts for the knot ring.

The position in which the above mentioned incision 27 is provided or the wire receiver 26 is secured is different from the pivoting position projecting inward in the radial direction horizontally or vertically and is a position near the pivoting position so that the pulled wire may act on the knot rings to effectively curve the insertion part.

By the way, as clear also from FIG. 1, the incised positions of the knot ring provided with the horizontal incisions 27 are opposed to each other as displaced by 90 degrees from these incisions 27 and the wire receivers 26 are secured respectively in these incisions.

The image guide 8 as an image transmitting means and the light guides 9 for transmitting illuminating lights can be inserted through the hollow inside the above mentioned knot rings 12. By the way, as shown in FIG. 4, the light guides are three so that the illuminating light amount may be larger.

Figure 8:
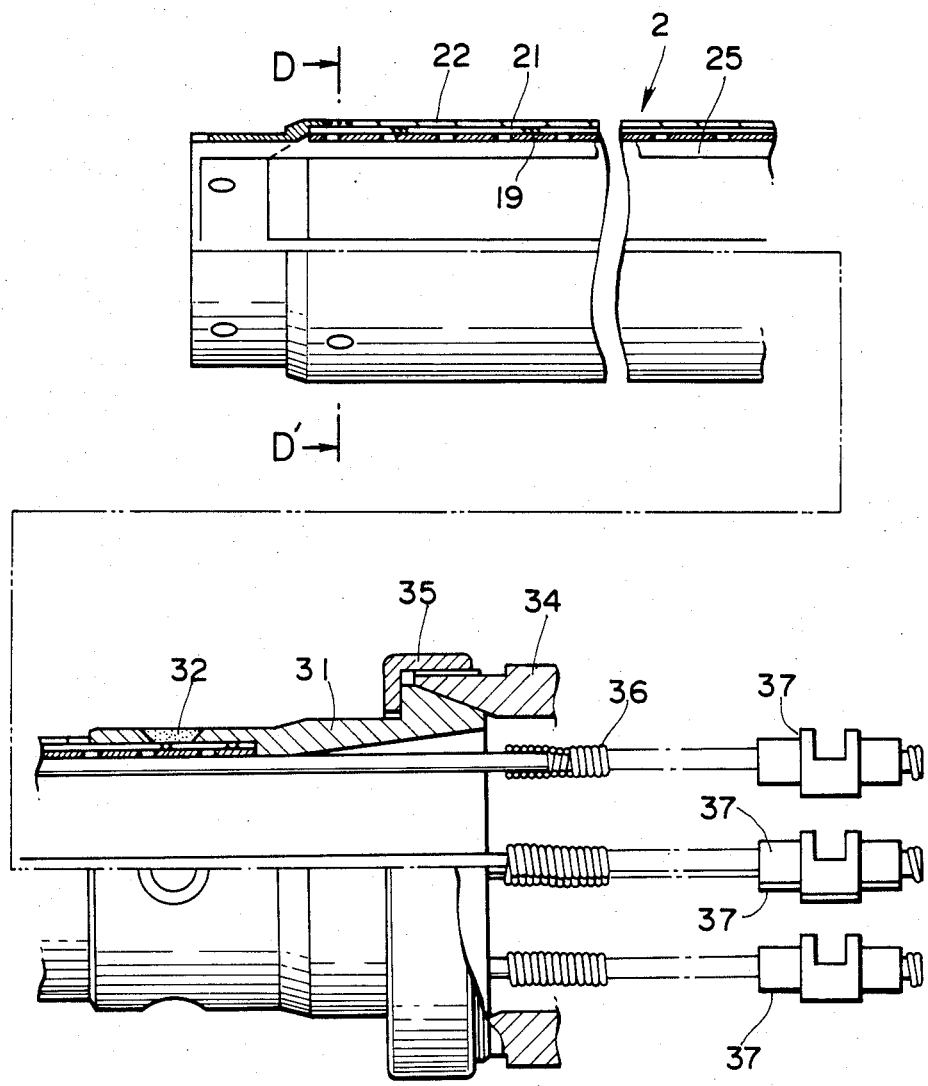

Now, the insertion part 2 on the rear side of the above mentioned curvable part 10 is of such structure as is shown in FIG. 8.

That is to say, the spiral tube 19 is covered with the net tube 21 which is further covered with the flexible tube 22. This net tube 21 is fitted at the rear end into a mouthpiece member 31 and is secured by pouring a solder 32 or the like into holes made on the outer peripheral surface of this mouthpiece member 31 which is fitted with a mouthpiece member 34 for connecting the operating part 3 and is secured with a fixing ring 35.

Figures 9, 12:
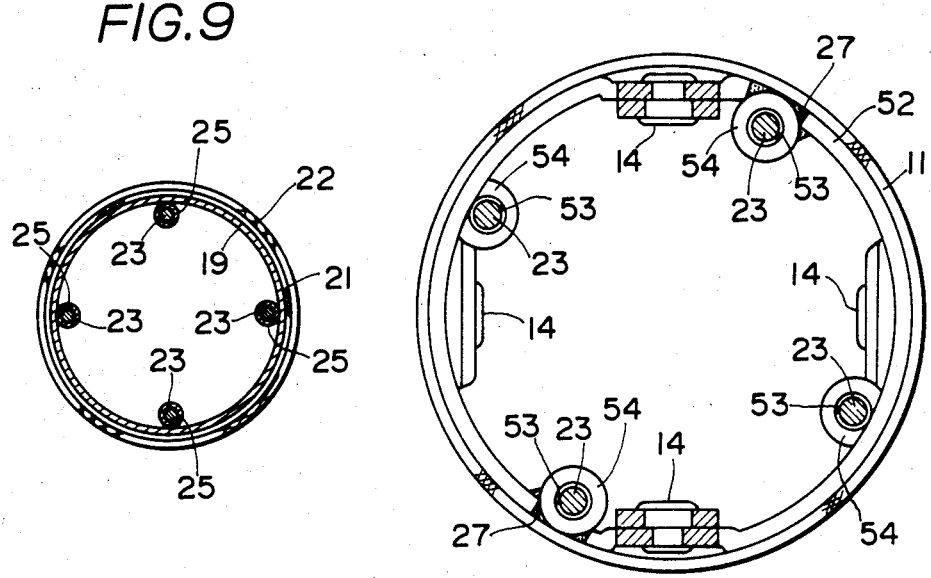
FIG. 12 is a sectioned view showing wire receivers secured to the knot rings forming the second embodiment.

The respective stainless steel pipes 25 through which the above mentioned respective wires 23 are inserted are passed in contact with the inner peripheral surface of the net tube 21 as shown in FIG. 9. As shown in FIG. 8, in the connecting part of both mouthpiece members 31 and 34 mentioned above, that is, the connecting part of the insertion part 2 and operating part 3, these stainless steel pipes 25 are replaced with coil pipes 36 wound on the rear ends of the stainless steel pipes 25. The respective coil pipes 36 are connected to the curving operation mechanism through relaxation removers 37 within the operating part 3.

According to the thus formed first embodiment, as a means of fitting the respective wire receivers 26 in the curvable part 10, the incisions 27 are made in the knot rings 12 and the wire receivers 26 are fitted and secured respectively in the incisions 27. Therefore, the amount of the projection of the wire receivers 26 projecting into the hollow inside the knot rings 12 can be made smaller and the effective cross-sectional area of the hollow path through which the image guide 8 and light guides 9 can be inserted can be made larger. Therefore, without enlarging the outside diameter of the insertion part 2 or curvable part 10, for example, the cross-sectional area of the fiber bundle of the light guide 9 can be made larger, therefore the illuminating light amount can be made larger and a clear observed image can be obtained.

In the case of using the device, without changing the outside diameter of the light guide 9, the outside diameter of the curvable part 10 can be made smaller, therefore the range in which the curvable part can be inserted and used can be made wider and, in the case of the endoscope to be inserted into a body cavity, the pain given to the patient can be reduced.

The above mentioned first embodiment is applied to an industrial endoscope as an endoscope device but it is evident that the present invention is not limited to it and can be applied to a medical endoscope. Further, as shown in FIG. 10, this embodiment can be applied also to an endoscope inserting auxiliary 41 as an endoscope device to make it easy to guide the tip side of the endoscope 1 to a target position.

Figure 10:
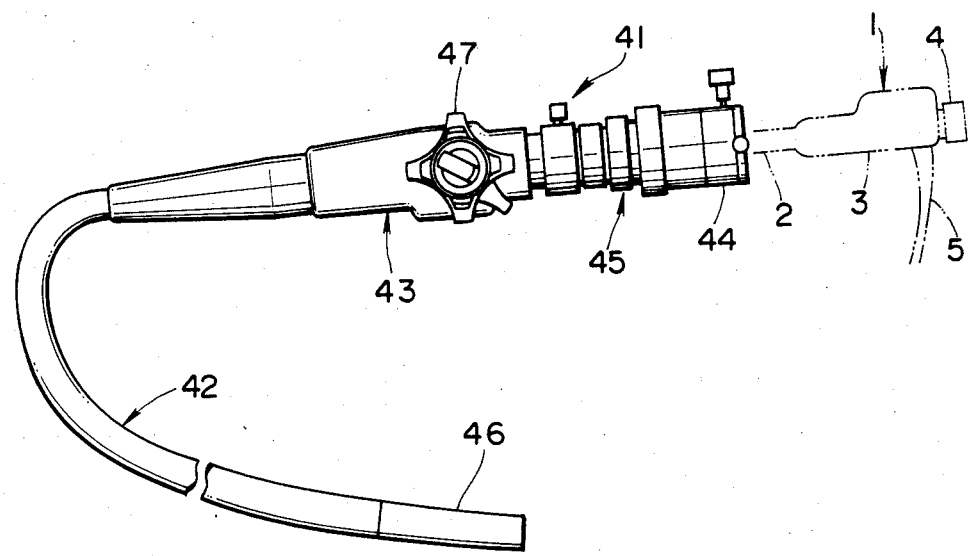
FIG. 10 is a perspective view showing the endoscope inserting auxiliary provided with the second embodiment.

As shown in FIG. 10, this auxiliary 41 is formed of an elongated guide tube part (hollow insertion part) 42 provided with a hollow path through which, for example, the insertion part 2 of the above mentioned endoscope 1 can be passed, a wide guide tube operating part 43 connected to the rear end side of this guide tube part 42, an endoscope fitting part 44 formed on the rear end side of this guide tube operating part 43 and fitted with the operating part 3 of the endoscope 1 and a telescopic endoscope holding part 45 formed between the above mentioned (guide tube) operating part 43 and endoscope fitting part 44.

Figure 11:
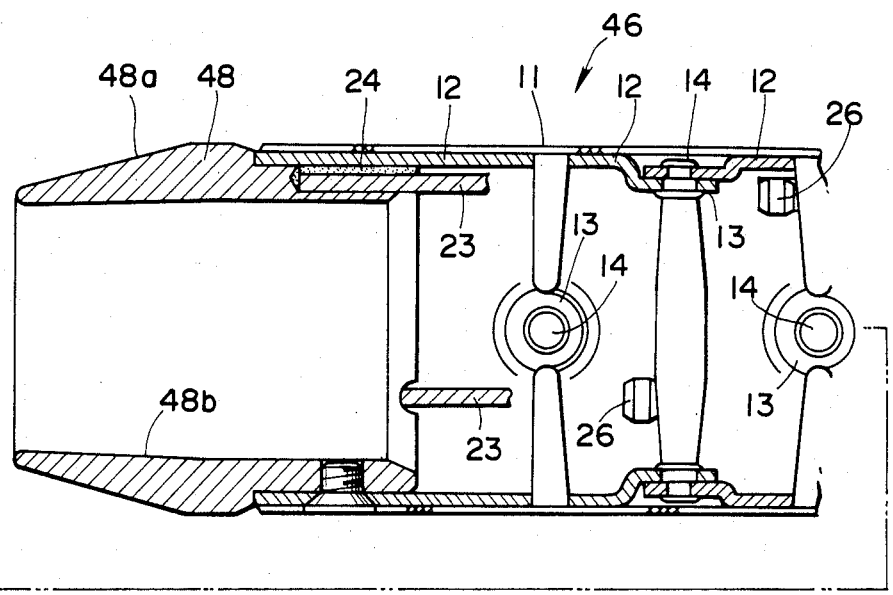
FIG. 11 is a sectioned view showing the structure of a curvable part provided on the tip side in FIG. 10.

On the tip side of the above mentioned guide tube part 42, as shown in FIG. 11, a curvable part 46 is formed so as to be curvable vertically or horizontally by rotating a curving operation knob 47 provided to project on the operating part 43.

In this curvable part 46, the tip part body 15 shown in FIG. 3 in the case of the above mentioned endoscope 1 is made a substantially cylindrical tip member 48 in which the tip side of the outer peripheral surface is made a tapered surface 48a tapered to be of a smaller diameter so as to be easy to insert into the inserting course and the tip side of the inner peripheral surface is also made a tapered surface 48b to be of a slightly smaller diameter so as to be easy to guide and insert on the inside the insertion part 2 of the endoscope 1 toward the center axis.

The tip member 48 is otherwise of the same structure as that in FIG. 3 when the fiber bundle of the image guide 8 and the fiber bundles of the light guides 9 are removed.

FIG. 12 shows a cross-section of a knot ring 52 forming the curvable part of the second embodiment of the present invention as sectioned in the jointing part position.

In each knot ring 52 of this second embodiment, the same as in the first embodiment, for example, the incisions 27 are made in two places opposed to each other and a wire receiver 54 in which a wire inserting hole 53 is formed eccentrically is secured in each incision 27 by a solder 55 or the like.

The above mentioned inserting hole 53 is formed eccentrically from the center axis of the cylinder of the wire receiver 54 and the wire receiver 54 is secured eccentrically so as to be thinner in the part opposed to the center axis of the knot ring 52. That is to say, the inserting hole 53 is made more toward the center axis of the knot ring 52 than in the case shown in FIG. 1. Each wire 23 passed through the inserting hole 53 of the wire receiver in this state is slightly away from the inner peripheral surface of the knot ring 52 so as to be hard to rub the inner peripheral surface of the knot ring 52 and to be easy to curve.

By the way, in FIG. 3, in the case of a medical endoscope, the net tube 11 may be covered on the outer peripheral surface with a flexible tube or the like or the knot rings may be covered with the flexible tube without using the net tube 11.

By the way, the wire receiver 26 may be not only ring-shaped having no cut but also C-ring-shaped or the like or may be square pillar-shaped in the contour provided with a circular inserting hole.

As described above, according to the present invention, as the knot rings forming the curvable part are provided with incisions in which the wire receivers may be fitted and secured respectively, the amount of the projection of the wire receivers projecting inside the knot rings can be made smaller and therefore the effective cross-sectional area of the hollow path inside the knot rings can be made larger. Thus, the outside diameters of the insertion part of the endoscope and the guide tube of the endoscope inserting auxiliary can be made smaller, the range of the applicability can be expanded and the pain given to the patient can be reduced in the case of a medical treatment.

By the way, the wire 23 for the curvable part may be fixed at the tip to the foremost knot ring 12 or to the tip part body 15.

What is claimed is:

1. In an endoscope device formed of at least one of an endoscope having an elongated insertion part capable of being inserted into a pipe cavity or body cavity and containing an observing means within said insertion part and an endoscope insertion auxiliary used to lead the insertion part of said endoscope to an object position and forming an elongated hollow insertion part through which said insertion part can be inserted, a curvable part device for said endoscope device comprising:

a plurality of substantially ring-shaped knot rings formed on the tip side of the insertion part and arranged along the longitudinal direction of said insertion part;

pivoting members jointing said respective knot rings at the ends rotatably with each other;

pairs of curving wires passed inside the respective knot rings and fixed at the ends to the knot ring in the foremost step or to a member to which said knot ring is fixed;

a curving operation mechanism to which said curving wires are fixed at the other ends so that, by the rotating operation, one of said curving wires may be relaxed and the other may be pulled to curve the jointed knot rings;

wire receiving members fixed to the inner peripheral sides of said knot rings and each provided with a wire inserting hole guiding said curving wire so as to be free to advance and retreat; and wire receiver fixing mechanisms wherein said wire receiving members are engaged partly and fixed in respective incisions formed in said knot rings to reduce the amount of the projection of the respective wire receiving members projecting radially inside from the inner peripheral surfaces of the knot rings.

2. A curvable part device for endoscope devices according to claim 1 wherein, by said wire receiver fixing mechanisms, the respective wire receiving members are so fixed that the outer surfaces of the respective wire receiving members in the parts engaged within the respective incisions may be substantially in contact the respective incisions mayh be substantially in contact with the outer peripheral surface of the knot ring.

3. A curvable part device for endoscope devices according to claim 1 wherein said wire receiving member has said wire inserting hole formed eccentrically from the center axis of said wire receiving member and said wire inserting hole is fixed eccentrically toward the center axis of the knot ring.

4. A curvable part device for endoscope devices according to claim 1 wherein said wire receiving member is annular or cylindrical.

5. A curvable part device for endoscope devices according to claim 1 wherein said wire receiver fixing mechanisms are formed in the positions approaching said pivoting members with respect to the center axis of said knot ring.

6. A curvable part device for endoscope devices according to claim 1 wherein said wire receiver fixing mechanisms are formed in the positions opposed to each other at an angle of about 180 degrees with respect to the center axis of said knot ring for the pair of the curving wires.

* * * * *